United States Patent
Eckhouse et al.

(10) Patent No.: US 8,709,011 B2
(45) Date of Patent: Apr. 29, 2014

(54) DIRECTED CURRENT FOR HAIR REMOVAL

(75) Inventors: Shimon Eckhouse, Haifa (IL); Tuvia Dror Kutscher, Shoham (IL)

(73) Assignee: Syneron Medical Ltd, Yokneam Illit (IL)

( * ) Notice: Subject to any disclaimer, the term of this patent is extended or adjusted under 35 U.S.C. 154(b) by 1205 days.

(21) Appl. No.: 12/376,067

(22) PCT Filed: Aug. 2, 2007

(86) PCT No.: PCT/IL2007/000968
§ 371 (c)(1),
(2), (4) Date: Nov. 10, 2009

(87) PCT Pub. No.: WO2008/015681
PCT Pub. Date: Feb. 7, 2008

(65) Prior Publication Data
US 2010/0114091 A1    May 6, 2010

Related U.S. Application Data

(60) Provisional application No. 60/834,791, filed on Aug. 2, 2006, provisional application No. 60/881,487, filed on Jan. 22, 2007.

(51) Int. Cl.
*A61B 18/14* (2006.01)
(52) U.S. Cl.
USPC ............................. 606/43; 606/36

(58) Field of Classification Search
USPC ............................. 606/32–34, 36, 41, 43, 44
See application file for complete search history.

(56) References Cited

U.S. PATENT DOCUMENTS

| | | | | |
|---|---|---|---|---|
| 2,727,132 | A * | 12/1955 | Hills | 219/223 |
| 4,321,926 | A * | 3/1982 | Roge | 606/36 |
| 5,509,916 | A * | 4/1996 | Taylor | 606/13 |
| 6,702,808 | B1 * | 3/2004 | Kreindel | 606/9 |
| 8,206,381 | B2 * | 6/2012 | Lischinsky et al. | 606/34 |
| 2004/0186466 | A1 | 9/2004 | Chornenky et al. | |
| 2008/0154247 | A1 * | 6/2008 | Dallarosa et al. | 606/3 |

FOREIGN PATENT DOCUMENTS

| | | |
|---|---|---|
| EP | 0528055 A1 | 2/1993 |
| WO | WO 83/02389 A1 | 7/1983 |
| WO | WO 99/34867 A1 | 7/1999 |

* cited by examiner

*Primary Examiner* — Michael Peffley
(74) *Attorney, Agent, or Firm* — Smith Risley Tempel Santos LLC; Gregory Scott Smith

(57) ABSTRACT

A device and system for applying a directed electrical current to heated hair, for at least damaging if not destroying the hair follicle with the electrical current. The current may optionally be AC or DC current. The device for hair treatment, may include a heat source; and a source of electricity for delivering a charge upon contact of the hair with the heat source. The heat source may include a filament. Further, the filament can be a wire of about 0.03 mm to about 0.2 mm in diameter and/or constructed from a nickel chrome alloy.

37 Claims, 8 Drawing Sheets

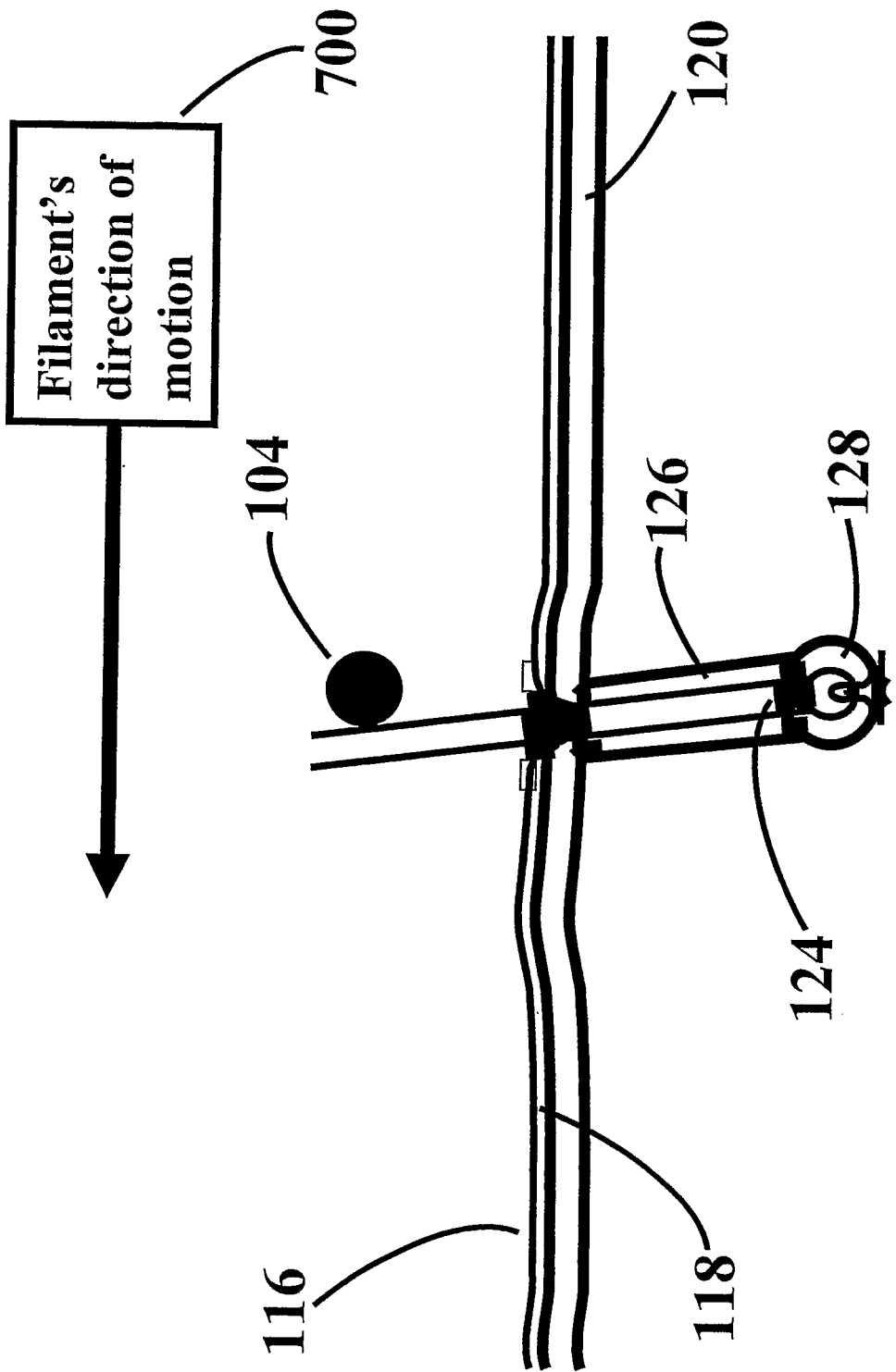

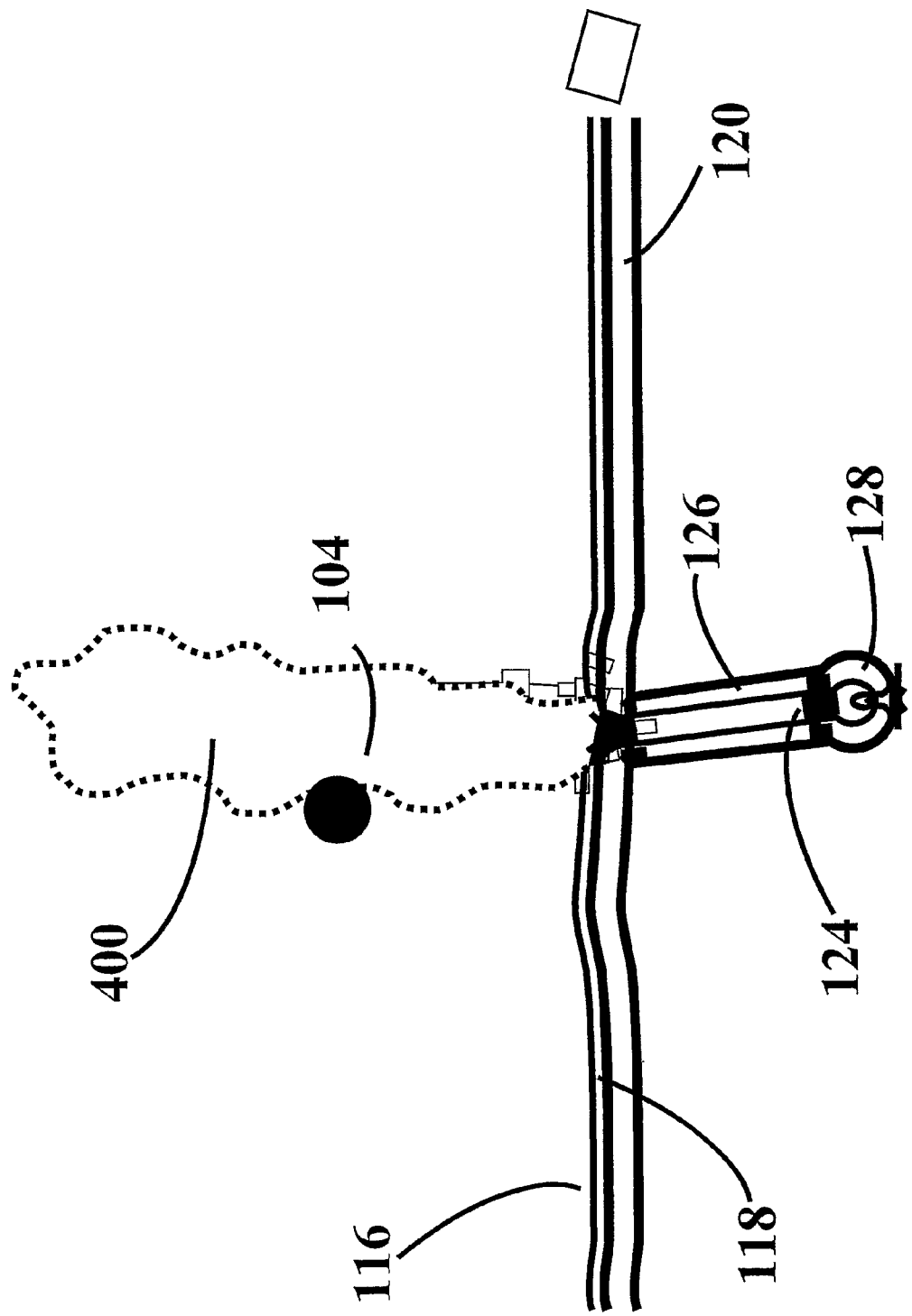

DIRECTED CURRENT FOR HAIR REMOVAL

CROSS-REFERENCE TO RELATED APPLICATIONS

This is a national phase application being filed under 35 USC 371 based upon, and claiming priority to International Application Number PCT/IL2007/000968 filed on Aug. 2, 2007, which application claims priority to U.S. Provisional Applications for Patent having Ser. No 60/834,791 and being filed on Aug. 2, 2006 and 60/881,487 and being filed on Jan. 22, 2007, all of which are hereby incorporated by reference in their entirety.

FIELD OF THE INVENTION

This invention relates to devices and methods for treating skin.

BACKGROUND OF THE INVENTION

Hair appears in many places on the human body. For cosmetic reasons, frequently individuals wish to remove the hair from certain body areas. Hair removal may be temporary, as for example through shaving, or permanent. Permanent hair removal requires destruction of the hair follicle itself; from which the hair grows. Each hair follicle is located in the dermis. The hair grows from the bottom of the hair follicle, from a location known as the dermal papilla. Without wishing to be limited by a single hypothesis, it is believed that the cells of the papilla must be destroyed in order to prevent the hair from growing back. However, its location in the lower dermis makes it more difficult to destroy without also destroying the skin tissue above and to the sides of the papilla. It has also been stated that hair growth is controlled by the bulge in the follicle that is typically located in the middle dermis; however, regardless of the location of the cells which control or promote hair growth, it is still necessary to penetrate deep enough into the skin to cause permanent hair (and tissue) damage.

Many different devices are available for hair removal by destroying the hair follicle. These devices generally suffer from a number of drawbacks. First, many such devices tend to cause damage to surrounding tissue. Second these devices are frequently difficult to apply optimally to destroy the hair follicle while still minimizing damage to surrounding tissue. As a result, a less skilled user can cause severe damage to the skin, for example by causing burns. The problem is particularly acute in that many devices rely upon electricity to destroy the hair follicle, which can easily also cause damage to surrounding tissues.

One example of such a device features a needle inserted into the hair follicle itself. High frequency electrical waves are then applied to the needle in an effort to destroy the hair producing papilla area. These types of devices are illustrated in U.S. Pat. Nos. 3,054,405 and 2,894,512. The insertion of the needle under the skin causes damage in various ways, as the needle itself causes irritation and swelling, while the application of electricity causes burning of the tissues. Also, needle based hair removal devices are limited by the speed of treatment. Since accurate insertion of the needle is critical in order to avoid unwanted damage to healthy tissue and to assure permanent damage to the hair follicle, it is very important that the operator be very accurate each time that the operator inserts the needle into the skin. This makes the electrolysis process lengthy, tedious and prone to human errors.

Other hair removal devices use an electrically charged tweezer which grips the hair above the skin and to which high frequency electrical waves are directly applied, such that the hair itself becomes a conductor to conduct electricity directly to the follicle. Such devices are shown in U.S. Pat. Nos. 4,174,713 and 5,026,369. Since this device does not use a needle, damage caused by the needle itself is avoided. However, this type of device is based on the assumption that hair conductivity is high enough to assure that electrical current reaches the hair follicle. In reality, human hair has a very high resistance and thus the electrical energy may not reach the hair follicle and destroy it to permanently block hair re-growth. Also, as this device requires the application of a strong electrical current near the skin, improper use of the device (by allowing the tweezer tip to contact the skin surface) may cause severe burns to surrounding skin tissue. Furthermore, the device must be applied separately to each hair, which is a painstaking and lengthy process, particularly for large areas of skin.

Other devices rely upon direct contact with the skin, but use some type of conductive lotion to guide electricity only to the hair follicle. Again, the hair itself is used a conductor, such that electricity is conducted down the hair to reach the hair follicle and destroy it. One example of such a device is disclosed in U.S. Pat. No. 5,522,814, which requires application of a conductive lotion. The lotion penetrates the pores of the skin and assists conduction of electricity to the hair follicle. However, this device still suffers from the drawbacks of the devices described above, in that electricity has to be conducted by the hair to the follicle, which, as noted above, is not very effective, due to the high resistance of hair. Furthermore, it may also easily cause damage to the surrounding skin, since current cannot be precisely pinpointed only to the hair follicle.

Even devices which attempt to treat only very small areas of the skin, such as those disclosed in U.S. Pat. No. 5,534,003, cannot pinpoint the hair follicle for treatment with electrical current, and hence cannot avoid damage to the surrounding skin tissue.

Other devices attempt to avoid any direct application of current to the skin, by using heated filaments located near the skin which burns the hair. For example, U.S. Pat. No. 2,727,132 discloses a device which features a heated filament and a skin guard to prevent contact between the filament and the skin, while still permitting the hair itself to be burnt. These devices may be configured so as to raise the heated filament away from the skin, thereby reducing the danger of burning the skin. However, they are not effective at destroying the hair follicle and hair re-growth can easily occur.

SUMMARY OF THE INVENTION

The above described background art devices clearly suffer from a number of drawbacks. Devices which are effective for destroying the hair follicle may easily cause severe damage to the surrounding skin tissue. Moreover, these devices must be used very slowly and are very limited in terms of their speed of operation since they require accurate positioning of the device at each hair. Devices which do not cause damage to the surrounding skin are not generally capable of destroying the hair follicle, so hair re-growth occurs. Clearly, a more useful device would pinpoint the hair follicle for application of electrical current without the need for accurate positioning by the operator while preventing the current from causing damage to surrounding skin tissue.

The present invention, in some embodiments, provides a device for applying a directed electrical current to heated hair, for at least damaging if not destroying the hair follicle with the electrical current. The current may optionally be AC or DC current.

According to some embodiments of the present invention there is provided a device for hair treatment, comprising: a. a heat source; and b. a source of electricity for delivering a charge upon at least contact of the hair with the heat source. Preferably, the heat source comprises a filament. More preferably, the filament comprises a wire of from about 0.03 mm to about 0.2 mm in diameter. Optionally and more preferably, the wire comprises a nickel chrome alloy.

Optionally, the heat source comprises an array of filaments.

Preferably the heat source burns the hair, and the device further comprises a detector for detecting burning of the hair. More preferably, the detector is selected from the group consisting of an optical detector, an acoustical detector and a detector for detecting a change in current and/or voltage. Most preferably, the heat source comprises a filament and the detector for detecting a change in current and/or voltage is electrically connected to the filament.

Preferably, the source of electricity comprises a pulse generator for generating a pulse of electricity.

Preferably, the pulse of electricity has a duration of from about 2 microseconds to about 100 milliseconds. More preferably, the pulse of electricity has a current of from about 1 mA to about 200 Amp with voltage in a range of from about 10V to about 500V.

Preferably, the heat source comprises a filament and wherein the pulse generator is electrically connected to the filament for delivering the pulse of electricity.

Optionally and preferably the device further comprises a housing for containing at least the heat source. Preferably, the housing further comprises a movable element for moving along the skin.

Optionally and preferably, the charge is delivered upon at least heating and preferably burning of the hair.

Also optionally and preferably the charge is delivered upon contact with the hair.

More preferably, the source of electricity is adapted such that the charge is delivered without direct contact between the source of electricity and the skin.

Optionally and preferably the device further comprises a spacer for maintaining a distance between the source of electricity and the skin. Preferably, the distance is in a range of from about 0.1 to about 5 mm. Optionally and preferably, the distance is adjustable through adjusting a position of at least one or both of the source of electricity and the spacer.

Optionally and preferably the device further comprises a spacer for maintaining a distance between the heat source and the skin. Preferably, the distance is in a range of from about 0.1 to about 5 mm. Also preferably, the distance is adjustable through adjusting a position of at least one or both of the source of electricity and the spacer.

Preferably the heating source comprises a filament and wherein source of electricity delivers the charge through the filament.

Optionally and preferably the device further comprises a guard for providing electrical insulation of the skin from the source of electricity.

According to other embodiments of the present invention, there is provided a device for hair treatment, comprising: a. a heat source for at least heating and preferably burning a hair; and b. a source of electricity for delivering a charge to the hair follicle.

According to still other embodiments of the present invention, there is provided a device for hair treatment, comprising: a. A heat source for at least heating a hair on skin of a subject; b. A source of electricity for delivering a charge upon at least contact of the hair with the heat source; c. A spacer for maintaining a distance between the source of electricity and the skin; and d. A housing for containing the heat source, the source of electricity and the spacer, wherein the housing is grippable. Optionally and preferably, the source of electrical energy is not in physical contact with the skin.

According to yet other embodiments of the present invention, there is provided a method of hair removal from skin of a subject, comprising: a. Contacting a hair with a heat source; b. Heating and preferably burning the hair; and c. Upon at least the contacting the hair, delivering an electrical charge to a follicle of the hair. Preferably, the charge is delivered upon burning of the hair. More preferably, the burning of the hair causes a column of hot gas to form and wherein the charge is delivered through the column of hot gas.

Preferably, the charge is delivered upon contacting the hair.

According to still other embodiments of the present invention, there is provided a method of hair removal from skin of a subject, comprising: a. Contacting a hair with a heat source; b. At least heating the hair; and c. Independently of the contacting the hair, delivering an electrical charge to a follicle of the hair.

Preferably the heating the hair comprises burning the hair.

Optionally and preferably the method further comprises applying a conductive material to the skin and/or hair shaft, prior to and/or during treatment.

Preferably, the electrical charge comprises an electrical pulse. More preferably, the electrical pulse is sufficiently strong for at least reducing hair re-growth. Most preferably, the electrical pulse is sufficiently strong for ablating a hair shaft and/or follicle.

According to yet other embodiments of the present invention, there is provided a method of hair removal from skin of a subject, comprising: a. Contacting a hair with the device as described herein; b. At least heating and preferably burning the hair; and c. delivering a directed electrical pulse to a follicle of the hair for at least reducing hair re-growth.

According to still other embodiments of the present invention, there is provided a device for hair treatment, comprising: a. A heat source for at least heating and preferably burning a hair; and b. A source of electrical energy which is not in physical contact with the skin.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 7 shows the direction of movement of heat source 104 as indicated with arrow 700; and FIG. 8 shows the consequence of the movement of heat source 104 as shown in FIG. 7, with hot gas 400 being formed as the hair is burnt.

DETAILED DESCRIPTION OF EMBODIMENTS

Figure 1:
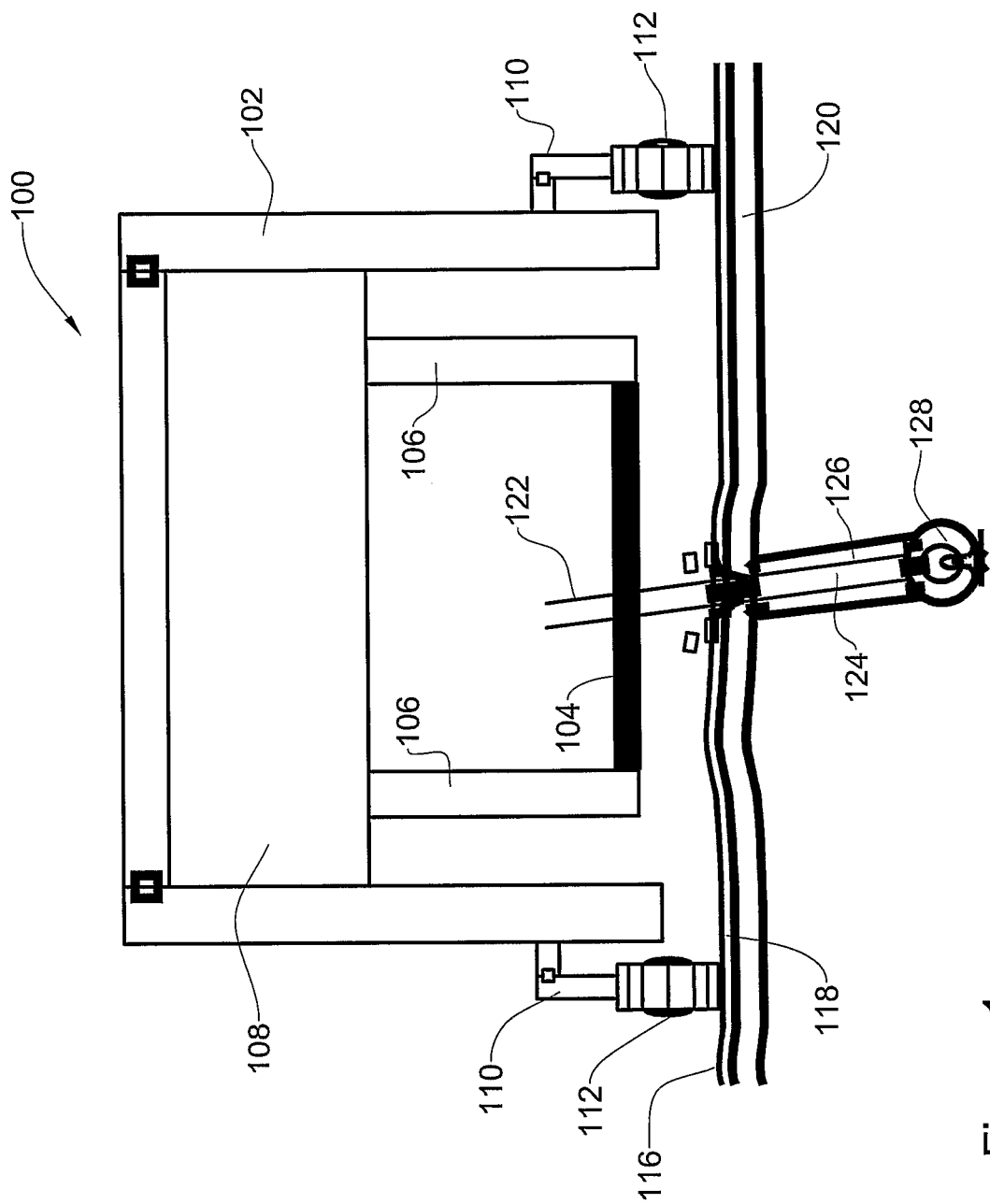
FIG. 1 shows a schematic diagram of at least a portion of a preferred embodiment of a device according to the present invention.

The present invention is of a device and method for hair removal and/or hair growth modification through the provision of a directed current. According to preferred embodiments of the present invention, an electrical current or optionally electric voltage, in either continuous wave or pulsed form, is applied to the hair only after the hair is at least heated using an outside heat source, as such an increase in temperature may be expected to lead to increased conductivity of the surrounding skin and/or the hair follicle and optionally also the hair shaft. Although the description below centers on hair ignition, it should be noted that this is for the purposes of illustration only and is not meant to be limiting in any way.

Optionally and preferably, the hair is ignited and performs a phase transition from its natural solid phase with very low electrical conductivity to a hot gas phase with very high electrical conductivity. This phase transition occurs by raising the hair temperature to a temperature that is higher than the ignition temperature of hair. The ignition process can also be used as a trigger for applying the electrical energy to the gaseous hair (following ignition and burning in the atmosphere). Once ignition is detected, an electrical current is applied to the burning hair and is conducted into the follicle. Therefore, preferably according to some embodiments the device of the present invention comprises a heating element that increases the temperature of an individual hair beyond ignition temperature and a sensor for detecting the presence of a hair and the set up of the ignition and burning of the hair and an electrical generator for generating a hair follicle damaging current upon detection of a burning hair by the sensor. The device also preferably comprises a current applicator for applying the current to the hair follicle. Optionally and preferably, a timer determines the length of time for which the hair follicle damaging current is to be applied to the hair follicle. As the application of current is triggered by the presence of a burning hair, skin surrounding the hair follicle should sustain little or no damage since the current enters the follicle through the high conductivity burning hair; once within the follicle, electricity is further conducted also by the lower shaft of the hair which is more moist and hence more conductive to electricity.

According to preferred embodiments of the present invention, a device is provided which comprises a filament for being heated, preferably constructed from material or materials having a suitable resistance, more preferably a metallic material or composite. The filament is such that it preferably reaches a temperature of approximately 800° C. or higher although a suitable temperature range is preferably from about 500° C. to about 1500° C. Optionally and preferably, a minimum temperature is about 450° C., which is the temperature at which the hair ignites and is burnt. The filament is held such that the filament is sufficiently above the skin to avoid damage to the skin surface, yet is able to contact a hair on the skin. Optionally and preferably, the filament is held by a holder that is part of a housing for incorporating the filament and for protecting the user from undesired or accidental contact with the filament; the holder itself (and/or the housing) is preferably separated from the skin by a spacer. An optional but typical separation distance is in the range of from about 0.1 to about 5 mm. Optionally and more preferably, the location of the filament is adjustable to accommodate different lengths of hair.

Upon heating of the filament and contacting of a hair by the filament, the filament ignites the hair which then burns, resulting in the generation of a column of hot gas. At the moment the hot filament creates contact with the hair, the filament is cooled down due to heat conduction into the hair, as hair itself has an extant heat capacity. This reduction in filament temperature causes the electrical resistance of the filament to decrease; this decrease can be detected easily by continuously measuring the voltage applied to the filament and the resulting current. Other optional but preferred methods of detecting ignition and detection of the hair can be based on the use of an optical detector at a proper wavelength range that detects the light emitted by the burning of the hair. Yet another detection method can optionally be based upon detection of the acoustic signal associated with the ignition and burning of the hair. The optical signal generated by the burning hair will be in the visible and infrared portion of the spectrum and can be easily detected by an optical detector including but not limited to a solid state photodiode, for example. Alternatively or additionally, since the burning of the hair produces rapidly expanding hot gases, it creates an acoustic signal that can be detected by a small piezo-electric detector for example, located in the vicinity of the filament.

One or more of these signals are optionally and preferably detected by a detector, which may optionally be adapted to detect an increase in current or decrease in voltage, optical signal or acoustic signal, or a combination of any two or more of such signals. The detector may optionally comprise a plurality of separate detectors and/or sensors adapted to a particular signal. The detector is connected to a current generator and preferably causes the current generator to deliver a short, intense burst of electrical energy to the filament (and/or alternatively to another conductive element) which is in contact with the hot gas resulting from the burning hair. The burning time of the hair may be in the range of from about tens of microseconds to about tens of milliseconds (for example and without intending to be limiting in any way, from about ten microseconds to about 200 milliseconds). As the column of hot gas has high conductivity and low resistance, the electricity is preferentially conducted to the hair follicle with the column of hot gas acting as a conductor. This short, intense burst of electricity then preferably damages the hair follicle, or at least one or more parts of the hair follicle and/or surrounding tissue which control, influence and/or promote the re-growth of hair. Alternatively, if no detector is used, the current generator may optionally operate periodically and/or continuously, given the difference in conductivity between hair that is burnt (ie hot gas) and hair that is not burnt.

Without wishing to be limited by a single hypothesis, this process is aided by the increase in temperature of the hair follicle and the tissue in its immediate vicinity, which further increases its conductance, thereby increasing the level of current delivered to the follicle. This positive feedback process of heating and increased conductance continues down the hair follicle and increases the probability of permanently damaging the hair follicle or at least one or more parts of the follicle and/or surrounding tissue which influence, promote and/or control hair growth.

Again without wishing to be limited by a single hypothesis, it is believed that in fact the hair shaft will continue to burn to a point below the surface of the skin, which may be approximately 0.25 mm below the skin (although the precise depth is not crucial for the operation of the present invention and may vary between individuals and between different hair types or different regions of skin being treated), at which point burning stops due to a lack of oxygen. The column of hot gas may therefore optionally continue to conduct electricity within the hair follicle below the surface of the skin, thereby further assisting in the process of ablating the hair follicle, again without wishing to be limited by a single hypothesis.

Although the term "filament" is used, it is understood that this may optionally encompass any suitable heat source for generating heat as described herein.

According to other preferred embodiments of the present invention, the device features a ground which optionally grounds the current on a separate portion of skin and/or alternatively on the device itself, so that a current loop is created which then permits the electrical current to be delivered to the hair follicle. Optionally and preferably, the short intense burst of electrical energy is generated by a pulse generator, which is controlled by a detector as described above for determining when the pulse generator generates the pulse. The energy for heating the filament is preferably provided by a filament power supply, which is electrically connected to the filament. Such a filament power supply may optionally be any suitable power supply, including but not limited to a DC (direct current) power supply, an AC (alternating current) power supply, fuel cell, a primary or a rechargeable electrochemical cell or any other type of suitable electrical power source known in the art.

According to still other preferred embodiments of the present invention, the device comprises a guard for preventing arcing of the short, intense burst of electrical energy to the skin. It is believed that the natural properties of the skin and hair, and of the surrounding air, may tend to minimize such an occurrence. The surrounding air acts as an insulator against the burst of electrical energy in comparison with the hot gas generated by the burning hair which is in immediate electrical contact with the filament.

According to other preferred embodiments of the present invention, the device comprises a plurality of filaments, each of which is preferably relatively short and each of which is preferably spaced apart. Without wishing to be limited in any way, an optional but typical length of each filament may be in the range of from about 1 cm to about 15 cm. The filaments may optionally be spaced in various ways at distances of a few cm. The distances between filaments are such that arcing between filaments is minimized. Each filament is preferably connected separately to the filament power supply and to the pulse generator, such that each filament may optionally receive a separate pulse at the appropriate moment when a hair is burnt to form hot gases. Similarly, each filament is preferably connected separately to the detector for detecting the ignition or burning of the hair. The length of each filament and the distances between filaments may optionally be adaptable according to the type of hair removal to be performed and the radius of curvature of the part of the body being treated. Also optionally, a filament may treat a plurality of hairs simultaneously or substantially simultaneously, such that references to "a hair" may be understood to optionally comprise a plurality of hairs.

The implementation of a device according to the present invention may vary depending upon the specific application. For example, the device of the present invention may optionally be implemented as a desktop or bedside system for use by a physician or cosmetician, or a home user or another user. Such a system may optionally include a main unit for housing some of the necessary electrical circuitry for providing power and control functions, safety functions and/or other components of the system and optionally a hand-held part which may be applied to the treated skin area and which may include a ground for the electrical current and the heating element or heat source, and optionally a sensor and the detector as described above. Optionally other additional components, including but not limited to, other sensors (for example for detecting the temperature of the surrounding skin) may be included.

According to optional but preferred embodiments of the present invention, a method for hair removal and preventing (or at least substantially reducing) hair re-growth comprises applying a heated filament to a hair, thereby burning the hair. The filament is preferably in physical contact with the hair. At the moment when the hair ignites and/or burns, various properties associated with the hair alter. One or more of these altered properties are optionally detected as previously described. A short, intense burst of electrical energy is then applied to the filament, which then preferably damages the hair follicle or at least one or more parts of the hair follicle that are involved in the control, promotion or influence of hair re-growth.

According to alternative embodiments of the present invention, at the moment when the hair first contacts the filament, such contact is optionally detected, followed by the application of an intense burst of electrical energy to the filament and/or to any other conducting element.

In any case, preferably the heated filament is slowly moved over the skin, so that a plurality of hairs are burnt and the above process is repeated a plurality of times. Optionally, the process may be repeated a plurality of times over a single area of skin, to be certain that all hairs and hair follicles have been treated. Also optionally, the method features visual inspection of the area of skin being treated by the user (which may optionally be a physician, nurse or other medical personnel, a trained user or the subject being treated), followed if necessary by passing the filament over the skin again.

According to optional embodiments of the present invention, electrically conductive material may optionally be applied to skin or hair shaft, or both, before or during operation of the device of the present invention. Without wishing to be limited to a single hypothesis, the application of such a material may improve coupling between the stratum corneum and applied electrical energy, so that the electrical energy may penetrate more deeply into the dermis and epidermis, and not remain in the stratum corneum area. The conducting material may optionally comprise any type of gel, solution and/or semi-solid which is capable of conducting electrical energy.

According to optional embodiments of the present invention, heat conductive material may optionally be applied to the hair shaft before or during operation of the device of the present invention. Without wishing to be limited to a single hypothesis, the application of such a material may improve the heat penetration via the hair shaft into hair follicle. The conducting material may optionally comprise any type of gel, solution and/or semi-solid which is capable of conducting heat energy, as for example various types of complex long chain polymers which are known in the art, including but not limited to PEG (polyethylene glycol), water and desalinated water, and the like.

The figures described below illustrate various non-limiting preferred embodiments of the present invention.

FIG. 1 shows a schematic diagram of at least a portion of a preferred embodiment of a device according to the present invention (the drawings given herein are highly schematic and are therefore more of a logic diagram; furthermore, components of the drawings are not necessarily shown to scale). As shown, a device 100 preferably features a holder 102 for holding a heat source 104 for being at least in close proximity to, and preferably, in contact with, a hair 126 of a patient. Hair 126 is shown as growing out of a schematic hair follicle 128, at least a portion of which is below a surface 116 of the skin (two skin layers are shown: epidermis 118 and dermis 120). Heat source 104 may optionally and preferably be constructed from any suitable material or combination of materials, such as a thin electrically conducting wire for example (including but not limited to a wire made of a nickel chrome alloy, or of any other suitable metallic or non-metallic electrically conducting material). According to preferred embodiments of the present invention, heat source 104 comprises a thin wire of from about 0.03 mm to about 0.2 mm in diameter.

Figure 3:
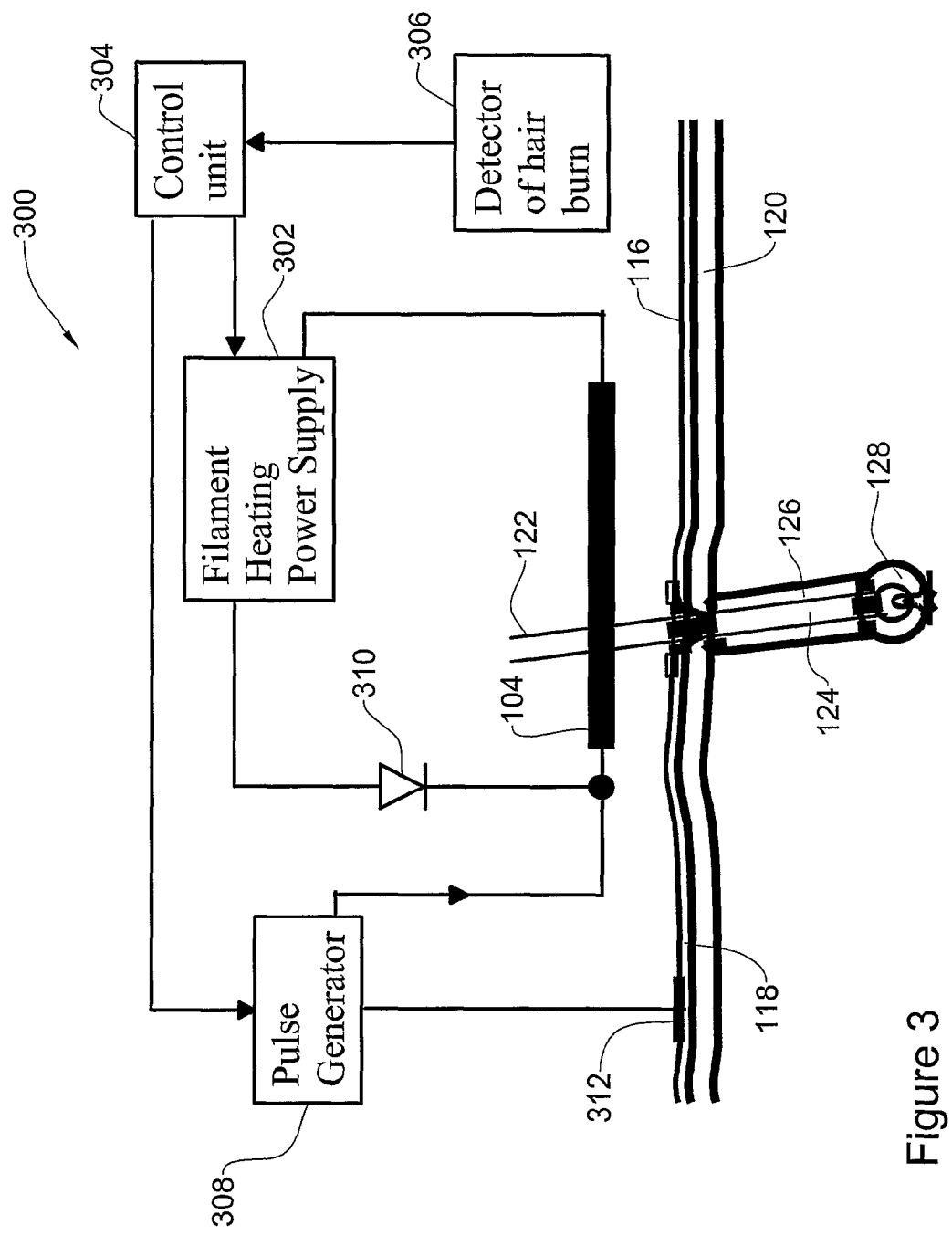
FIG. 3 is a schematic block diagram of an electrical circuit for optional but preferred embodiments of the device of the present invention.

Heat source 104 is preferably connected to a power supply 108, which as previously described may optionally be any suitable power source, including but not limited to a DC (direct current) power supply, an AC (alternating current) power supply, fuel cell, a primary or a rechargeable electrochemical cell or any other type of suitable electrical power source known in the art. Power supply 108 preferably supplies energy to heat source 104 so that heat source 104 becomes heated to a temperature that is preferably sufficiently high to ignite and burn hair 126. When the heat source 104 is a conducting wire as described above, the heat source 104 is part of an electrical circuit including the power supply 108, as shown in FIG. 3. In this case, the power supply 108 delivers a current through the heating element 104 in order to heat the heating element to the required temperature, which is optionally at or above the ignition temperature of hair. As heat source 104 initiates contact with hair 126, as noted previously, the resistance of heat source 104 changes which in turn affects the level of voltage and current, which can optionally be measured. Heat source 104 is preferably connected to power supply 108 by a connector 106.

For ease of movement along surface 116 of the skin by the operator of device 100, holder 102 is preferably connected to a plurality of movable elements 112 for moving along surface 116. More preferably, movable elements 112 comprise wheels or rollers as shown. Movable elements 112 are preferably connected to holder 102 by a movable element support 110, which may optionally permit movable elements 112 to be placed slightly to the side of holder 102 as shown.

According to preferred embodiments, when heat source 104 causes hair 126 to burn (or alternatively as described herein when heat source 104 contacts hair 126), a short pulse of electrical current is preferably delivered. Without wishing to be limited by a single hypothesis, such a pulse may more easily be conducted down the column of hot gas, as an upper portion 122 of hair 126 itself is dry and is not a good conductor. As the electricity is conducted down the column of hot gas, it may again be more easily conducted by a lower portion 124 of hair 126, which is more moist and has more electrolytes, and/or by hair follicle 128, again without wishing to be limited by a single hypothesis. Alternatively it may be expected (again without wishing to be limited by a single hypothesis) that heating hair 126 may cause hair 126, and/or surrounding skin and/or hair follicle 128, to be better conductors.

Figure 2:
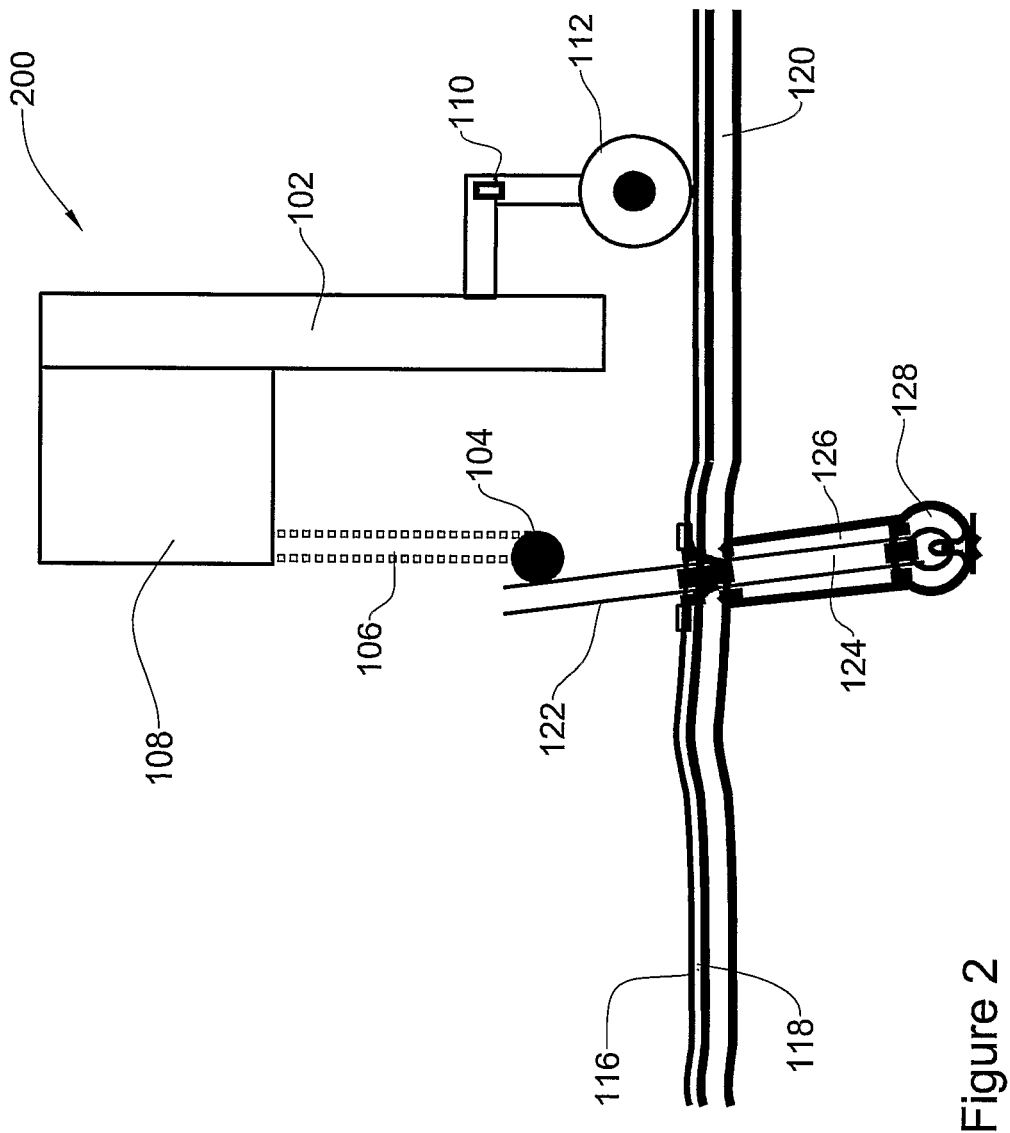
FIG. 2 shows a schematic diagram of the device of FIG. 1 in a side view.

FIG. 2 shows a schematic diagram of the device of FIG. 1 in a side view (the device is labeled as device 200). For this and subsequent drawings, elements with reference numbers that are repeated are similar or identical to those in previous drawings, unless otherwise noted. Optional but preferred contact between heat source 104 and upper portion 122 of hair 126 is shown for the purposes of illustration only and without any intention of being limiting.

FIG. 3 is a schematic block diagram of an electrical circuit for optional but preferred embodiments of the device 300 of the present invention. Heat source 104 is preferably connected to a power supply 302, which in turn is preferably connected to a control unit 304. A detector 306 is also optionally and preferably connected to control unit 304. Detector 306 preferably detects the change in current and/or voltage. Optionally additionally or alternatively, detector 306 detects an optical signal (from ignition of hair 126) or an acoustic signal (as hair 126 ignites and burns). Detector 306 then preferably communicates with control unit 304 (actively or passively), which preferably causes a pulse generator 308 to generate a short intense burst of electrical energy. Duration of the pulse may preferably vary in the range of from about 2 microseconds to about 100 milliseconds, while currents may be in the range of from about 1 mA to about 200 Amp with voltage in the range of from about 10V to about 500V. Pulse generator 308 is preferably electrically connected to heat source 104 such that heat source 104 delivers the short intense burst of electrical energy to the hot gas column (in place of hair 126) and hence to hair follicle 128. Preferably, at least a portion of hair follicle 128 is damaged and is more preferably ablated; optionally and preferably at least one or more portion or portions of hair follicle 128 that are related to control or promotion of, or influence on, hair re-growth are damaged (not shown).

Control unit 304 more preferably controls the level of current generated by one or both of power supply 302 and pulse generator 308.

Also, the electrical circuit optionally and preferably features a diode 310 for permitting current flow in only one direction.

A ground 312 is optionally in contact with surface 108 of the skin, so that a complete circuit is formed, with electricity being conducted to hair follicle 128 down the hot gases which form in place of hair 126. If high frequency current (more than 1 MHz) is used, ground 312 may optionally be eliminated, since the capacitive impedance of the body of the patient may optionally be sufficiently low to close the current loop. Alternatively, the ground may optionally be in contact with another portion of the device (not shown).

Figure 4:
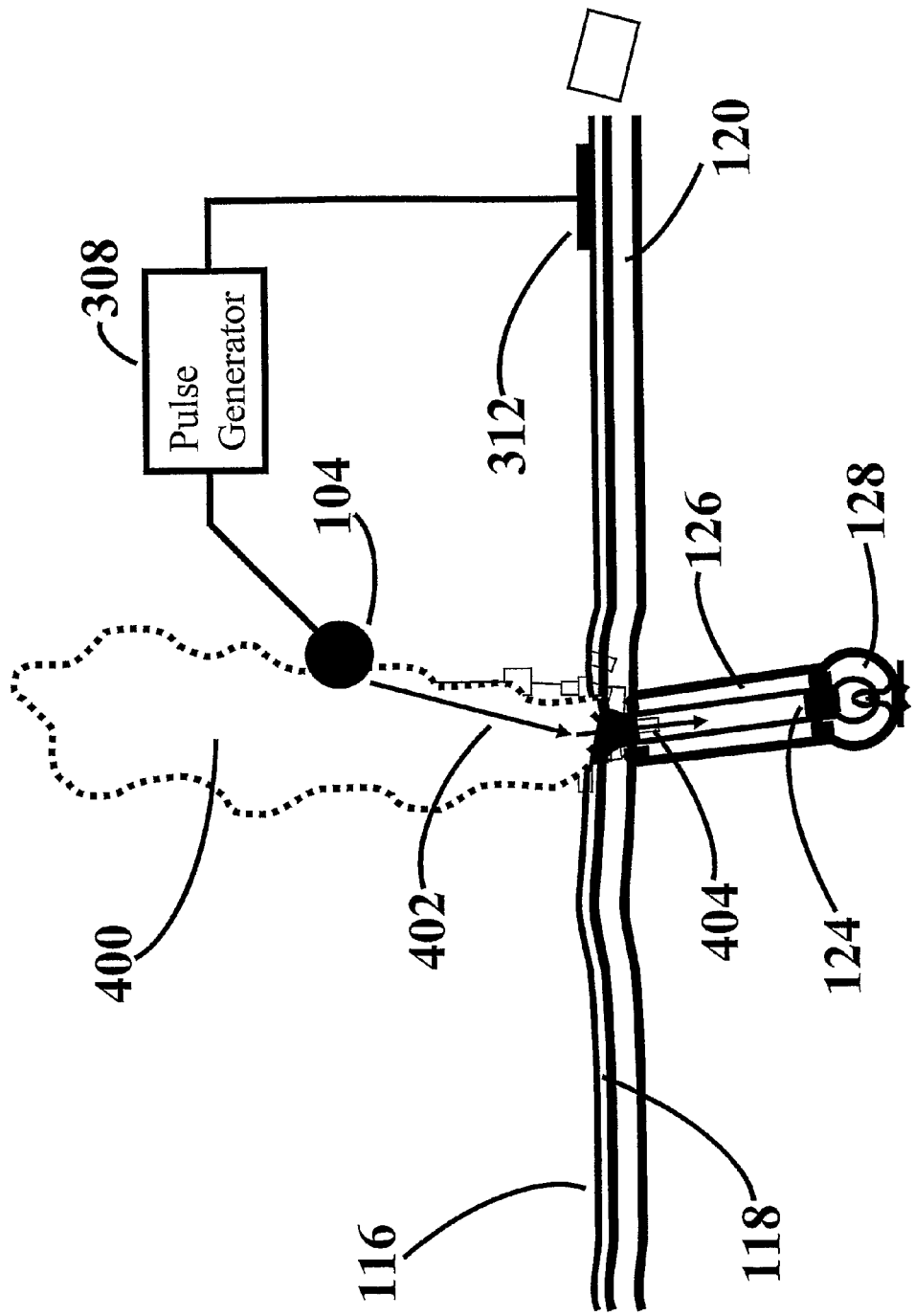
FIG. 4 shows only a portion of the schematic block diagram of FIG. 3.

FIG. 4 shows only a portion of the schematic block diagram of FIG. 3, for the sake of clarity only. As shown, upon burning of hair 126, a column or cloud of hot gas 400 is formed, which permits the electrical current generated by pulse generator 308 to be conducted to lower portion 124 of hair 126, as shown schematically by an arrow 402, and hence to follicle 128, as shown schematically by an arrow 404.

Figure 5:
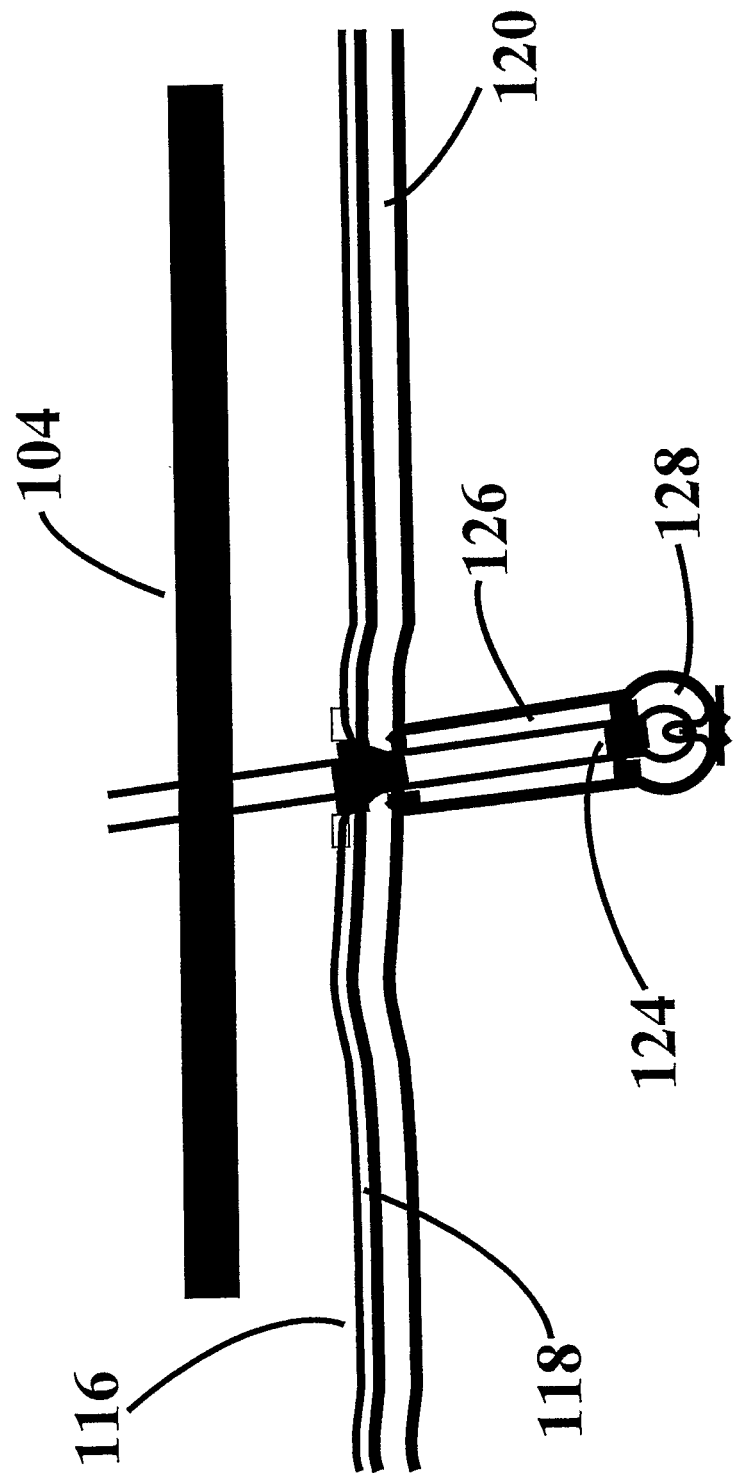
FIG. 5 shows only a portion of the schematic diagram of FIG. 1, showing heat source 104 contacting the hair.
Figure 6:
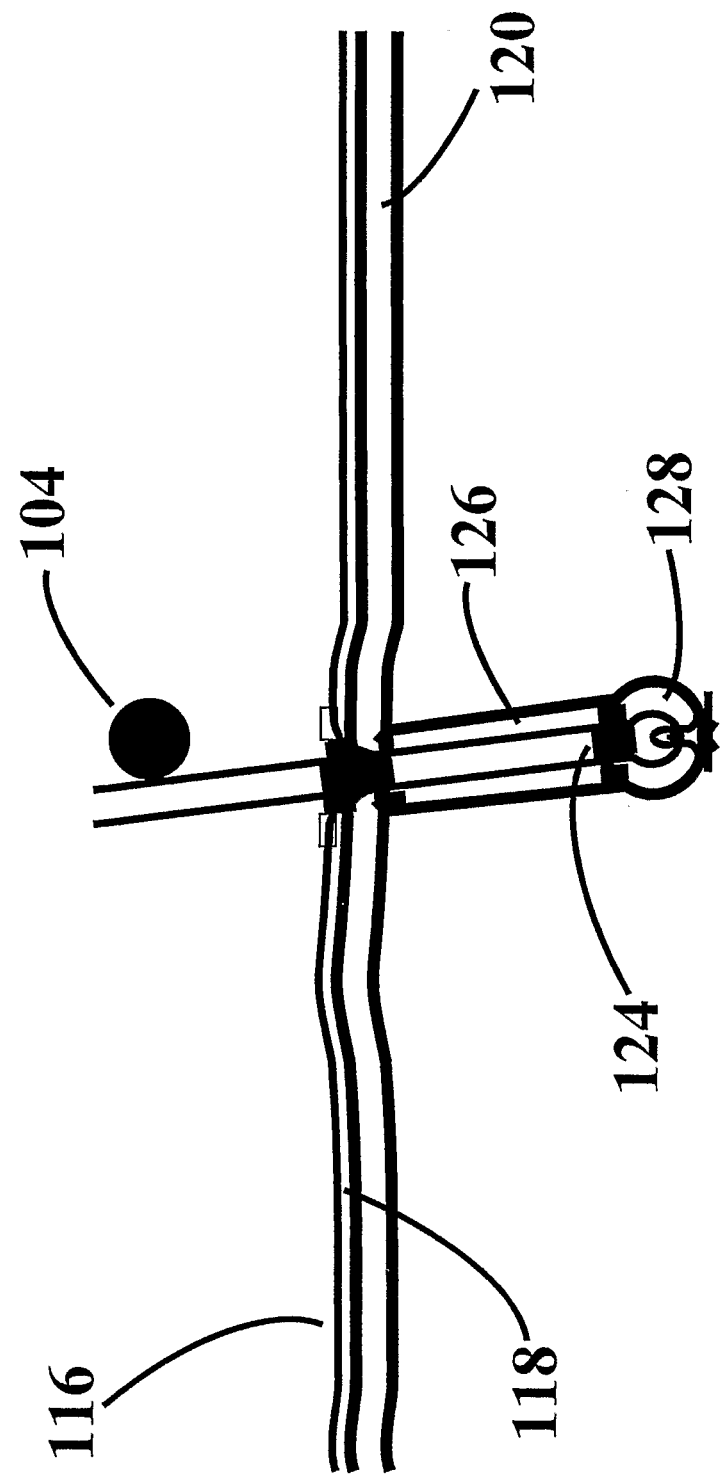
FIG. 6 shows the same portion but from a side view only.

FIG. 5 shows only a portion of the schematic diagram of FIG. 1, for the sake of clarity only, showing heat source 104 contacting the hair. FIG. 6 shows the same portion but from a side view only.

FIG. 7 shows the direction of movement of heat source 104 as indicated with arrow 700. FIG. 8 shows the consequence of the movement of heat source 104 as shown in FIG. 7, with hot gas 400 being formed as the hair is burnt.

While the invention has been described with respect to a limited number of embodiments, it will be appreciated that many variations, modifications and other applications of the invention may be made.

The invention claimed is:

1. A device for hair treatment, comprising:
    a heat source configured to ignite and burn at least one hair and form a hot gas column terminated at the hair follicle; and
    a source of electricity configured to deliver a charge through the hot gas column to the follicle and destroy at least partially the follicle;
    wherein the source of electricity is electrically connected to the heat source and configured to deliver a pulse of electricity.

2. The device according to claim 1, wherein the device further comprises a detector configured to detect a burning of the hair and communicate the burning of the hair with the source of electricity.

3. The device according to claim 2, wherein the device further comprises a control unit configured to communicate with the detector and with the source of electricity.

4. The device according to claim 2, wherein the detector is at least one detector selected from a group consisting of an optical detector, an acoustical detector and a detector for detecting a change in current or voltage or a combination thereof.

5. The device according to claim 2, wherein the detector is electrically connected to the heat source.

6. The device according to claim 1, wherein the heat source is a filament.

7. The device according to claim 1, wherein the heat source comprises an array of filaments.

8. The device according to any of claim 6 or 7, wherein the heat source is filament comprising a wire of from about 0.03 mm to about 0.2 mm in diameter.

9. The device according to any of claim 6 or 7, wherein the heat source filament is a nickel chrome alloy wire.

10. The device according to claim 1, wherein the source of electricity comprises a pulse generator configured to deliver a pulse of electricity.

11. The device according to claim 10, wherein the pulse of electricity has a duration of from about 2 microseconds to about 100 milliseconds.

12. The device according to claim 10, wherein the pulse of electricity has a current of from about 1 mA to about 200 Amp with voltage in a range of from about 10V to about 500V.

13. The device according to claim 1, wherein the heat source comprises a filament and wherein the source of electricity is configured to deliver the charge through the filament.

14. The device according to claim 1, wherein the hot gas column conducts electricity.

15. The device according to claim 1, wherein the charge is delivered upon at least contact with the hair.

16. The device according to claim 1, wherein the charge is delivered upon at least heating and preferably burning of the hair.

17. The device according to claim 1, wherein the charge is delivered upon at least detection of the burning of the hair.

18. The device according to claim 1, wherein the source of electricity is configured so the charge is delivered without direct contact between the heat source and the skin.

19. The device according to claim 1, further comprising a housing configured to contain at least the heat source.

20. The device according to claim 19, wherein the housing further comprises a movable element configured to move over the skin.

21. The device according to claim 1, further comprising a spacer configured to maintain a distance between the heat source and the skin.

22. The device according to claim 21, wherein the distance is adjustable through adjusting a position of at least one or both of the heat source and the spacer.

23. The device according to claim 21, wherein the distance is in a range of from about 0.1 to about 5 mm.

24. The device according to claim 1, further comprising a guard configured to provide electrical insulation of the skin from said source of electricity.

25. A device for hair treatment, comprising:
    a heat source configured to ignite and burn at least one hair on skin of a subject and preferably form a hot gas column;
    a source of electricity configured to deliver a charge to the hair follicle through a filament, and
    a detector configured to detect a burning of the hair and communicate the burning of the hair with the source of electricity.

26. The device according to claim 25, wherein the hot gas column conducts electricity.

27. A method for hair removal from skin, said method comprising the steps of:
    providing a heat source, electrically connected to a pulse generator, configured to ignite and burn at least one hair and form a hot gas column terminating at the hair follicle;
    providing a detector configured to detect the burning of the hair and to communicate the burning of the hair to a control unit controlling at least the pulse generator;
    generating a pulse of electrical charge by the pulse generator, delivering it to the hot gas column and damaging at least one hair follicle.

28. A method of hair removal from skin of a subject, comprising the steps of:
    contacting at least one hair with a heat source;
    at least heating and burning the hair; and
    delivering an electrical charge through the heating and burning source to a follicle of the hair.

29. The method according to any of claim 27 or 28, further comprising the step of applying a conductive material to the skin or hair shaft, prior to or during treatment or a combination thereof.

30. The method according to any of claim 27 or 28, wherein the step of delivering an electrical charge further comprises providing an electrical pulse sufficiently strong for at least reducing hair re-growth.

31. The method according to any of claim 27 or 28, wherein the step of delivering electrical charge further comprises providing an electrical pulse sufficiently strong for ablating a hair shaft or follicle or combination thereof.

32. A method of hair removal from skin of a subject, comprising the steps of:
    contacting a hair with the device comprising:
    a heat source that ignites and burns at least one hair and forms a hot gas column;
    a source of electricity configured to deliver a charge, and
    a detector configured to detect a burning of the hair and communicate the burning of the hair with the source of electricity;
    at least heating and substantially burning the hair, and
    delivering a directed electrical pulse to a follicle of the hair at least reducing hair re-growth; and using the source of electricity to deliver through the heat source a directed electrical pulse to a follicle of the hair to at least substantially burn the hair and reduce hair re-growth.

33. The method according to claim 32, wherein the hot gas column conducts electricity.

34. A method of hair removal from skin of a subject, comprising the steps of:
enabling transition of at least one hair from natural solid phase into a hot gas phase by contacting it with a hot filament and forming a hot gas column;
detecting the transition of the hair from natural solid phase into a hot gas phase and generating the hair follicle damaging current; and
conducting the hair follicle damaging current to the follicle through the hot filament and permanently damaging the hair follicle.

35. The method according to claim 34, wherein the step of conducting the hair follicle damaging current is performed such as not to damage the surrounding the follicle skin.

36. The method according to claim 35, wherein the step of detecting the transition of the hair from natural solid phase into a hot gas phase is detected by at least one detector selected from a group consisting of an optical detector, an acoustical detector and a detector for detecting a change in current or voltage or a combination thereof.

37. A device for hair treatment comprising:
a heat source configured to ignite and burn at least one hair on skin of a subject and preferably form a hot gas column;
a source of electricity configured to deliver a charge or a pulse of electricity to the hair follicle through a filament; and
a detector configured to detect a burning of the hair and communicate the burning of the hair with the source of electricity.

* * * * *